(12) United States Patent
Zhao (10) Patent No.: US 10,210,737 B2
(45) Date of Patent: Feb. 19, 2019

(54) SYSTEMS AND METHODS FOR PRIVACY-AWARE MOTION TRACKING WITH NOTIFICATION FEEDBACK

(71) Applicant: Cleveland State University, Cleveland, OH (US)

(72) Inventor: Wenbing Zhao, Avon, OH (US)

(73) Assignee: Cleveland State University, Cleveland, OH (US)

( * ) Notice: Subject to any disclaimer, the term of this patent is extended or adjusted under 35 U.S.C. 154(b) by 217 days.

(21) Appl. No.: 15/190,669

(22) Filed: Jun. 23, 2016

(65) Prior Publication Data

US 2016/0381328 A1 Dec. 29, 2016

Related U.S. Application Data

(60) Provisional application No. 62/183,515, filed on Jun. 23, 2015.

(51) Int. Cl.
| | |
|---|---|
| *H04N 7/18* | (2006.01) |
| *G08B 21/04* | (2006.01) |
| *G06K 9/00* | (2006.01) |
| *G06F 3/01* | (2006.01) |
| *G06T 7/246* | (2017.01) |
| *G06T 7/73* | (2017.01) |

(52) U.S. Cl.
CPC ......... *G08B 21/0446* (2013.01); *G06F 3/016* (2013.01); *G06F 3/017* (2013.01); *G06K 9/00342* (2013.01); *G06K 9/00355* (2013.01); *G06T 7/246* (2017.01); *G06T 7/73* (2017.01); *G06T 2207/10016* (2013.01); *G06T 2207/30196* (2013.01); *G06T 2207/30232* (2013.01); *G06T 2207/30241* (2013.01)

(58) Field of Classification Search
CPC ................................................. G08B 13/19602
USPC .................................................. 348/142–160
See application file for complete search history.

(56) References Cited

U.S. PATENT DOCUMENTS

2016/0086462 A1 * 3/2016 Meganathan ..... G06F 17/30843
348/155

OTHER PUBLICATIONS

A. Garg and J. M. Kapellusch, "Long-term efficacy of an ergonomics program that includes patient-handling devices on reducing musculoskeletal injuries to nursing personnel," Human Factors: The Journal of the Human Factors and Ergonomics Society, vol. 54, No. 4, pp. 608-625, 2012.

(Continued)

*Primary Examiner* — Anand S Rao
(74) *Attorney, Agent, or Firm* — Calfee, Halter & Griswold LLP; Joshua Friedman; Christopher Jackson (57) ABSTRACT

Systems and methods to perform privacy-aware computer-vision-based human activity monitoring with real-time haptic feedback. The system and method described in this disclosure employing a registration process for consenting human subjects before their activities are monitored. The registration process involves the corroboration of human motion captured in different modalities, i.e., computer-vision-based via the programmable computer-vision-based motion sensor and accelerometer-based via the wearable device. The tracked human activities are assessed in real-time and upon detection of activities that violated predefined rules, haptic feedback is delivered in real-time to the tracked human subject via the wearable device worn by the caregiver.

20 Claims, 5 Drawing Sheets

(56) References Cited

OTHER PUBLICATIONS

B. D. Owen, K. Keene, and S. Olson, "An ergonomic approach to reducing back/shoulder stress in hospital nursing personnel: a five year follow up," International journal of nursing studies, vol. 39, No. 3, pp. 295-302, 2002.
H. J. Lim, T. R. Black, S. M. Shah, S. Sarker, and J. Metcalfe, "Evaluating repeated patient handling injuries following the implementation of a multi-factor ergonomic intervention program among health care workers," Journal of safety research, vol. 42, No. 3, pp. 185-191, 2011.
W. Zhao, D. D. Espy, M. Reinthal, and Fl Feng, "A feasibility study of using a single kinect sensor for rehabilitation exercises monitoring: A rule based approach," in Computational Intelligence in Healthcare and e-health (CICARE), 2014 IEEE Symposium on. IEEE, 2014, pp. 1-8.
W. Zhao, R. Lun, D. D. Espy, and M. Reinthal, "Rule based realtime motion assessment for rehabilitation exercises," in Computational Intelligence in Healthcare and e-health (CICARE), 2014 IEEE Symposium on. IEEE, 2014, pp. 133-140.
W. Zhao, R. Lun, D. D. Espy, and M. Ann Reinthal, "Realtime motion assessment for rehabilitation exercises: Integration of kinematic modeling with fuzzy inference," Journal of Artificial Intelligence and Soft Computing Research, vol. 4, No. 4, pp. 267-285, 2014.
T. Gropelli and K. Corle, "Assessment of nurses and therapists occupational musculoskeletal injuries," Medsurg Nursing, vol. 20, No. 6, 2011.
(2012) http://www.osha.gov/SLTC/healthcarefacilities/index.htm. Department of Labor.
S. Mohammed, "Evaluation of occupational risk factors for Nurses and Cnas: Analysis of Florida workers compensation claims database," Ph.D. dissertation, University of South Florida, 2013.
E. Velloso, A. Bulling, and H. Gellersen, "Motionma: motion modelling and analysis by demonstration," in Proceedings of the SIGCHI Conference on Human Factors in Computing Systems. ACM, 2013, pp. 1309-1318.
J.-S. Lin and D. Kulic, "Online segmentation of human motion for automated rehabilitation exercise analysis," Neural Systems and Rehabilitation Engineering, IEEE Transactions on, vol. 22, No. 1, pp. 168-180, 2014.
S. Nomm and K. Buhhalko, "Monitoring of the human motor functions rehabilitation by neural networks based system with kinect sensor," in Analysis, Design, and Evaluation of Human-Machine Systems, vol. 12, No. 1, 2013, pp. 249-253.
T. Hachaj and M. R. Ogiela, "Rule-based approach to recognizing human body poses and gestures in real time," Multimedia Systems, vol. 20, No. 1, pp. 81-99, 2014.
J. N. Katz, "Lumbar disc disorders and low-back pain: socioeconomic factors and consequences," The Journal of Bone & Joint Surgery, vol. 88, No. suppl 2, pp. 21-24, 2006.
W. S. Marras, S. A. Lavender, S. E. Leurgans, S. L Rajulu, W. G. Allread, F. A. Fathallah, and S. A. Ferguson, "The role of dynamic three-dimensional trunk motion in occupationally-related low back disorders: The effects of workplace factors, trunk position, and trunk motion characteristics on risk of injury." Spine, vol. 18, No. 5, pp. 617-628, 1993.
A. Avci, S. Bosch, M. Marin-Perianu, R. Marin-Perianu, and P. Havinga, "Activity recognition using inertial sensing for healthcare, wellbeing and sports applications: A survey," in Proceedings of the 23rd international conference on Architecture of computing systems. VDE, 2010, pp. 1-10.
R. Lun and W. Zhao, "A survey of applications and human motion recognition with microsoft kinect," International Journal of Pattern Recognition and Artificial Intelligence, vol. 29, No. 5, p. 1555008, 2015.
T. Videman and M. C. Batti'e, "Spine update: the influence of occupation on lumbar degeneration," Spine, vol. 24, No. 11, 1164-1168, 1999.

F. A. Fathallah, W. S. Marras, and M. Parnianpour, "The role of complex, simultaneous trunk motions in the risk of occupation-related low back disorders," Spine, vol. 23, No. 9, pp. 1035-1042, 1998.
A. K. Burton, "Back injury and work loss: biomechanical and psychosocial influences," Spine, vol. 22, No. 21, pp. 2575-2580, 1997.
R. M. Araujo, G. Grana, and V. Andersson, "Towards skeleton biometric identification using the microsoft kinect sensor," in Proceedings of the 28th Annual ACM Symposium on Applied Computing. ACM, 2013, pp. 21-26.
B. C. Munsell, A. Temlyakov, C. Qu, and S.Wang, "Person identification using full-body motion and anthropometric biometrics from kinect videos," in Computer Vision-ECCV 2012. Workshops and Demonstrations. Springer, 2012, pp. 91-100.
J. Wu, J. Konrad, and P. Ishwar, "Dynamic time warping for gesture-based user identification and authentication with Kinect," in Acoustics, Speech and Signal Processing (ICASSP), 2013 IEEE International Conference on. IEEE, 2013, pp. 2371-2375.
R. Kannavara and K. L. Shippy, "Topics in biometric human-machine interaction security," Potentials, IEEE, vol. 32, No. 6, pp. 18-25, 2013.
J. Preis, M. Kessel, M. Werner, and C. Linnhoff-Popien, "Gait recognition with kinect," in 1st international workshop on kinect in pervasive computing, 2012.
H. Debar and A. Wespi, "Aggregation and correlation of intrusion-detection alerts," in Recent Advances in Intrusion Detection. Springer, 2001, pp. 85-103.
B. Morin, L. Me, H. Debar, and M. Ducasse, "A logic-based model to support alert correlation in intrusion detection," Information Fusion, vol. 10, No. 4, pp. 285-299, 2009.
F. Valeur, G. Vigna, C. Kruegel, R. Kemmerer et al., "Comprehensive approach to intrusion detection alert correlation," IEEE Transactions on Dependable and Secure Computing, vol. 1, No. 3, pp. 146-169, 2004.
M. Hravnak, L. Edwards, A. Clontz, C. Valenta, M. A. DeVita, and M. R. Pinsky, "Defining the incidence of cardiorespiratory instability in patients in step-down units using an electronic integrated monitoring system," Archives of internal medicine, vol. 168, No. 12, pp. 1300-1308, 2008.
O. Chipara, C. Lu, T. C. Bailey, and G.-C. Roman, "Reliable clinical monitoring using wireless sensor networks: experiences in a step-down hospital unit," in Proceedings of the 8th ACM Conference on Embedded Networked Sensor Systems. ACM, 2010, pp. 155-168.
M. Roesch et al., "Snort: Lightweight intrusion detection for networks." in Proceedings of the 13th Systems Administration Conference, vol. 99, No. 1, Seattle, WA, 1999, pp. 229-238.
D. L. Hayes and P. A. Levine, "Pacemaker timing cycles," in Cardiac pacing and ICDs. Blackwell Publishing Malden (MA), 2002, pp. 265-321.
P. Wang, A. Kramer, N. Estes, and D. L. Hayes, "Timing cycles for biventricular pacing," Pacing and clinical electrophysiology, vol. 25, No. 1, pp. 62-75, 2002.
C. Cobelli and E. Carson, Introduction to modeling in physiology and medicine. Academic Press, 2008.
R. Sommer and V. Paxson, "Outside the closed world: on using machine learning for network intrusion detection," in Proceedings of the IEEE Symposium on Security and Privacy. IEEE, 2010, pp. 305-316.
V. A. Convertino, S. L. Moulton, G. Z. Grudic, C. A. Rickards, C. Hinojosa-Laborde, R. T. Gerhardt, L. H. Blackbourne, and K. L. Ryan, "Use of advanced machine-learning techniques for noninvasive monitoring of hemorrhage," Journal of Trauma and Acute Care Surgery, vol. 71, No. 1, pp. S25-S32, 2011.
A. King, K. Fortino, N. Stevens, S. Shah, M. Fortino-Mullen, and I. Lee, "Evaluation of a smart alarm for intensive care using clinical data," in Proceedings of the Annual International Conference of the IEEE Engineering in Medicine and Biology Society. IEEE, 2012, pp. 166-169.
P. K. Murukannaiah and M. P. Singh, "Platys: An active learning framework for place-aware application development and its evaluation," ACM Transactions on Software Engineering and Methodology, pp. 1-33, 2015.

(56) References Cited

OTHER PUBLICATIONS

K. Townsend, C. Cufi, A. Davidson, and R. Davidson, Getting Started with Bluetooth Low Energy: Tools and Techniques for Low-Power Networking. O'Reilly Media, 2014.
W. Zhao, D. D. Espy, M. Reinthal, B. Ekelman, G. Goodman, and J. Niederriter, "Privacy-aware human motion tracking with realtime haptic feedback," in Proceedings of the IEEE International Conference on Mobile Services. IEEE, 2015, pp. 446-453.
State of the media: Trends in tv viewing2011 tv upfronts, 2011.
T. Choudhury, S. Consolvo, B. Harrison, J. Hightower, A. Lamarca, L. LeGrand, A. Rahimi, A. Rea, G. Bordello, B. Hemingway, et al. The mobile sensing platform: An embedded activity recognition system. Pervasive Computing, IEEE, 7(2):32-41, 2008.
J. Doyle, A. Kealy, J. Loane, L. Walsh, B. O'Mullane, C. Flynn, A. Macfarlane, B. Bortz, R. B. Knapp, and R. Bond. An integrated home-based self-management system to support the wellbeing of older adults. Journal of Ambient Intelligence and Smart Environments, 6(4):359-383, 2014.
R.-E. Fan, P.-H. Chen, and C.-J. Lin. Working set selection using second order information for training support vector machines. The Journal of Machine Learning Research, 6:1889-1918, 2005.
A. Fleury, M. Vacher, and N. Noury. Svm-based multimodal classification of activities of daily living in health smart homes: sensors, algorithms, and first experimental results. Information Technology in Biomedicine, IEEE Transactions on, 14(2):274-283, 2010.
C.-W. Hsu, C.-C. Chang, and C.-J. Lin. A practical guide to support vector classification. 2010.
A. Jalal and S. Kamal. Real-time life logging via a depth silhouette-based human activity recognition system for smart come services. In Advanced Video and Signal Based Surveillance (AVSS), 2014 11th IEEE International Conference on, pp. 74-80. IEEE, 2014.
A. D. Lopez, C. D. Mathers, M. Ezzati, D. T. Jamison, and C. J. Murray. Global and regional burden of disease and risk factors, 2001: systematic analysis of population health data. The Lancet, 367(9524):1747-1757, 2006.
G. Mastorakis and D. Makris. Fall detection system using kinect's infrared sensors. Journal of Real-Time Image Processing, pp. 1-12, 2012.
M. Skubic, R. D. Guevara, and M. Rantz. Testing classifiers for embedded health assessment. In Impact Analysis of Solutions for Chronic Disease Prevention and Management, pp. 198-205. Springer, 2012.
E.-E. Steen, T. Frenken, M. Eichelberg, M. Frenken, and A. Hein. Modeling individual healthy behavior using home automation sensor data: Results from a field trial. Journal of Ambient Intelligence and Smart Environments, 5(5):503-523, 2013.
C.-J. Su, C.-Y. Chiang, and J.-Y. Huang. Kinect-enabled home-based rehabilitation system using dynamic time warping and fuzzy logic. Applied Soft Computing, 22:652-666, 2014.
J. Wen, M. Zhong, and J. Indulska. Creating general model for activity recognition with minimum labelled data. In Proceedings of the 2015 ACM International Symposium on Wearable Computers, pp. 87-90. ACM, 2015.
W. Zhao, H. Feng, R. Lun, D. D. Espy, and M. Reinthal. A kinect-based rehabilitation exercise monitoring and guidance systems. In Proceedings of the 5th IEEE International Conference on Software Engineering and Service Science, pp. 762-765. IEEE, 2014.

\* cited by examiner

SYSTEMS AND METHODS FOR PRIVACY-AWARE MOTION TRACKING WITH NOTIFICATION FEEDBACK

CROSS-REFERENCE TO RELATED APPLICATIONS

This application claims benefit to U.S. Provisional Patent Application No. 62/183,515, filed Jun. 23, 2015, which is hereby incorporated by reference herein in its entirety.

INTRODUCTION

The present disclosure generally relates to the field of motion tracking of users. More specifically, the present disclosure is directed to systems and methods of utilizing motion sensors, wearable devices, and smart phones, to perform human motion tracking with real-time haptic feedback, such as an alarm or a tactile indication based on tracked activities of the user. The system may be designed to improve job performance of a user, reduce likelihood of injuries, and/or to alert a user of an otherwise improper movement and/or posture. The disclosure additionally relates to methods and systems to respect privacy concerns of other individuals that are proximate to the tracked user, thereby avoiding improper data collection of data due to the privacy concern and governmental regulations. The disclosure further relates to novel methods for registering a user utilizing motion detection in conjunction with other technologies. Systems and method disclosed herein allow for real-time feedback to a user so that the user may be warned of potential injuries and/or other improper activities before they occur.

BACKGROUND

Computer-vision based human motion tracking has undergone intensive research for the past several decades. Today, inexpensive portable computer-vision based motion sensors can now be used to accurately track human motions. Such technology could includes benefits. For example, many of the work-related injuries could have been prevented or minimized if the workers follow best practices (such as using proper lifting equipment and following proper gaits and postures).

Computer-vision based human motion tracking technology could be used to track workers' activities and detect violations of best practices. A system based on the technology could provide instant alerts, for example, via vibration and message notification on the display of the wearable device worn by the worker in this case, and therefore, could potentially reduce the occurrences of such violations in the future.

Unfortunately, such computer-vision based technology can rarely used in workplaces, particularly in venues such as hospitals and nursing homes, to monitor workers' activities because of privacy-related governmental regulations such as such as the Health Insurance Portability and Accountability Act of 1996 (HIPAA). Even if a worker has consented to being monitored, a vision-based motion sensor cannot guarantee that only the consenting person is tracked due to the indiscriminative nature of the computer-vision technology itself: anyone in its view might be automatically tracked.

Inertial sensor-based devices, such as wearable devices, can be used to track some form of human activity, such as steps taken, while preserving the privacy of those who are not wearing such devices. However, only a small set of such devices cannot be used to accurately track more sophisticated human activities that involve multiple joints and where trajectory of the movement matters. Furthermore, although multi-modal motion tracking based on both computer-vision and inertial sensors has been explored previously, it is used solely used to improve the accuracy of the motion tracking itself, not to enable the tracking of specific human subjects.

What is needed is a system and method that enables the monitoring of only consenting human subjects, which preserves the privacy of those who have not consented.

SUMMARY

Systems and methods to facilitate privacy-aware human activity monitoring are provided herein. A consenting human subject will be required to wear a programmable wearable device, such as a smart watch. One or more programmable computer-vision based motion sensors, such as a Microsoft Kinect sensor, will be used to track the activities of the consenting human subject. Discriminative tracking is achieved by a registration mechanism executed when the human subject enters the view of a camera and periodically while the subject stays in the view. The registration mechanism identifies the consenting subject in the view of the camera by matching a predefined gesture that is simultaneously captured by both the wearable device and the computer-vision based motion sensor. After the registration step, only the consenting subject is tracked and the motion data collected for all non-consenting subjects will be discarded immediately. Before the initial registration step, a frame supplied by the motion sensor is dropped immediately, or only a finite set of most recent frames are cached for the purpose of registration.

The system has also mechanisms that remind and guide the consenting human subject to register (in case he/she forgets to register) and to register properly (in case he/she did not come to the view of the motion sensor). The system sends alerts to the consenting human subject upon detection of violations of best practices via the wearable device worn by the subject using haptic feedback (i.e., vibrations) and text-based notifications (on the screen display of the wearable device).

In one aspect, a system to monitor only consenting human subjects is provided and includes one or more computer-vision based programmable motion sensors, one or more programmable wearable devices, one or more smart phones, and one or more processors. The one or more computer-vision based programmable motion sensors identify a consenting human subject that is wearing one of the programmable wearable devices and identify a non-consenting human subject. The one or more processors ignore the non-consenting human subject and monitor the consenting human subject for violations of best practices and provide violation alerts to the consenting human subject when a violation is detected. Such a system may also include a wristband having a reflective material which is worn by consenting human subjects and the one or more computer-vision based programmable motion sensors identify the human subject by identifying the wristband.

In another aspect, a system for alerting a person of improper actions is provided and includes a plurality of motion sensors that communicate to send a stream of images of a viewing area of the motion sensors, a wearable device that is associated with the user and capable of sending and receiving a signal indicative of the person in a field of view of the motion sensors, and a central processor that receives the signal from the wearable device indicating the presence of the person in the viewing area, monitors the images from the motion sensors to identify the person, tracks one or more orientations of the person, identifies an improper orientation, and sends a warning signal based on the identified improper orientation.

In still another aspect, a method for identifying a consenting human subject is provided and includes recognizing via one or more sensors a predefined gesture performed by a consenting human subject who is wearing a detectable wearable device, providing a registration request including an indication that the consenting human subject has interest in being monitored, receiving vision-based motion data from one or more motion sensors, recognizing a gesture by the consenting human subject from the vision-based motion data, and providing a confirmation message to the consenting human subject via haptic feedback a short message displayed on the wearable device. The gesture may be a tapping motion on the wearable device by one or more fingers of the opposite hand which is detected by one or more accelerometers in the wearable device and compared against a predefined configurable threshold.

In yet another aspect, a method for alerting a person of improper actions is provided and includes receiving from one or more user devices an indication that a user is present in a viewing area, activating in response to the indication one or more motion sensors to monitor the viewing area, receiving the image data from the one or more sensors, analyzing the image data to identify the user, tracking the movements of the user based on the image data, identifying a posture that is indicative of potential harm to the user, and sending a warning signal to one or more alert systems.

DETAILED DESCRIPTION

This Detailed Description merely describes exemplary embodiments of the invention and is not intended to limit the scope of the claims in any way. Indeed, the invention as claimed is broader than the exemplary embodiments, and the terms used in the claims have their full ordinary meaning, unless an express definition is provided herein.

Figure 9:
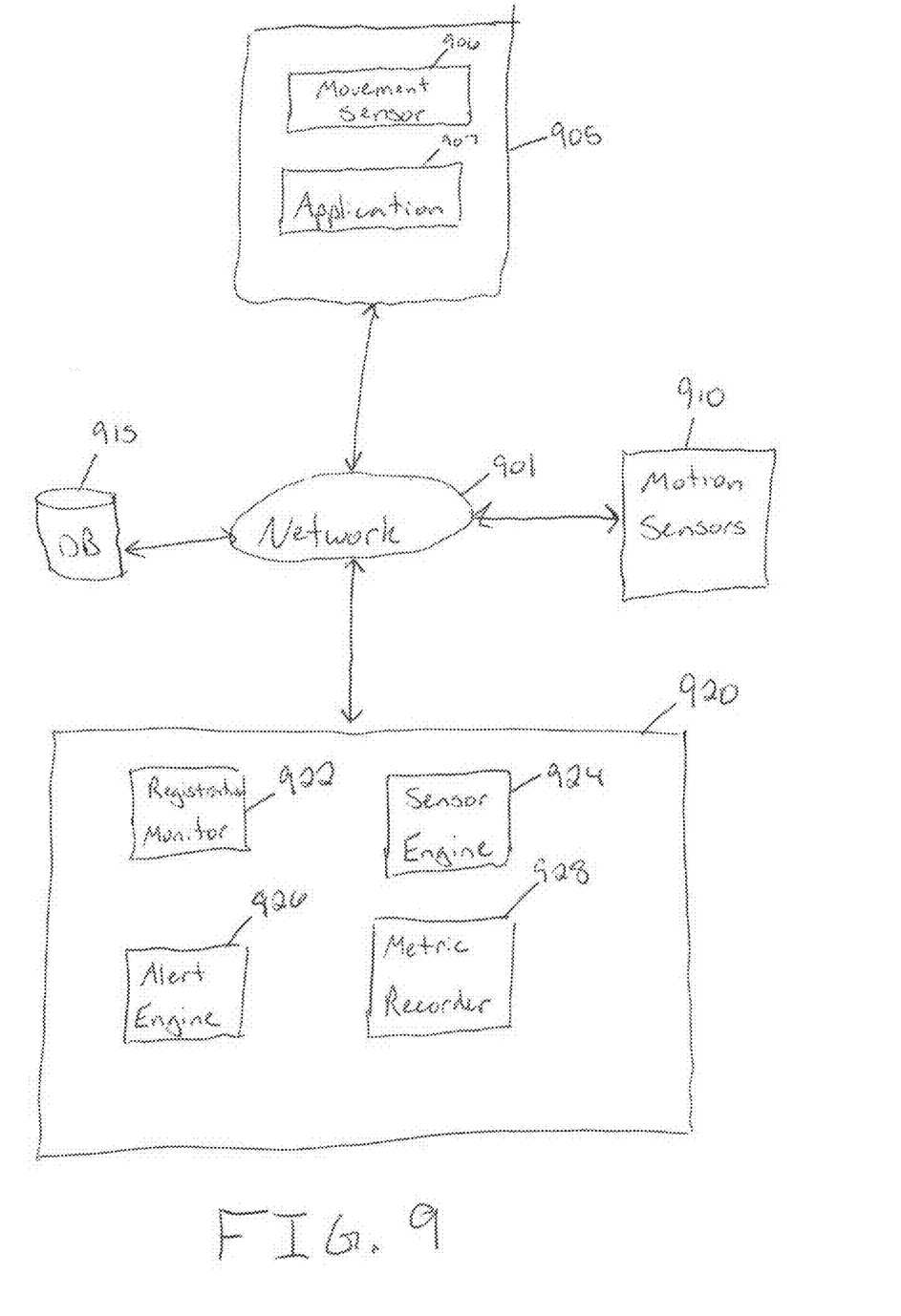
FIG. 9 is a block diagram of an example environment is provided in which privacy-aware motion tracking may be performed.

Referring to FIG. 9, a block diagram of an example environment is provided in which privacy-aware motion tracking may be performed. The environment includes a network communication 901. The communication network 901 facilitates communication between the various components in the environment. In some implementations, the communication network 901 may include the Internet, one or more intranets, and/or one or more bus subsystems. The communication network 901 may optionally utilize one or more standard communications technologies, protocols, and/or inter-process communication techniques. For example, network communication 901 may include communication via Wi-Fi, BLUETOOTH, RF, and/or one or more alternate communication protocols. The example environment also includes personal device 905, which may include, for example, a cellular phone, a smart phone, a tablet computing device, and/or one or more wearable devices (e.g., a fitness tracking device, a smart watch, an electronic tag). The personal device 905 may include one or more movement sensors 906 that may record movements of a user that is associated with the wearable device 906. For example, movement sensors 906 may include accelerometers, gyroscopes, location sensors, and/or one or more other sensors that can detect movements of the associated user. Personal device 905 may additionally be executing one or more applications 907. Applications 907 may include one or more applications associated with executing, analyzing, processing, and/or transmitting data from movement sensors 906. Additionally or alternatively, applications 907 may include one or more components of the system described herein. For example, one or more of the components described as components of system 920 may be executing, wholly or in part, on personal device 905.

Motion sensors 910 include one or more components that transmit image data to one or more components. In some implementations, motion sensors 910 may analyze image data to identify objects that are in proximity to the motion sensor 910. For example, referring to FIG. 1, motion sensors 102 and 104 may each emit a signal to identify objects within the view of the sensors. For example, an image of worker 130 and/or one or more objects nearby worker 130 may be identified by sensors 102 and 104 via, for example, image data, infrared data, and/or one or more other visual image identification protocols.

Referring again to FIG. 9, the environment includes a database 915. Database 915 may store information related to one or more users of the system 920. For example, database 915 may include login information, user biometrics (e.g., body size, joint locations, facial feature information), and/or other user data. In some implementations, one or more user records in database 915 may be associated with additional information related to past sessions of the user interacting with the system. For example, a record for a user may include information related to movements that were observed by motion sensors 910 in previous sessions and/or movements of the user that were identified by movement sensors 906.

System 920 includes one or more components that work in conjunction with other components of the example environment to identify a user that is visible to motion sensors and track movements of the user in a privacy-aware environment. In some implementations, one or more of the component and/or steps performed by system 920 may additionally and/or alternatively be performed on one or more other computing devices. For example, one or more of the components illustrated as part of system, 920 may be performed by personal device 905, motion sensors 910, and/or one or more other computing devices (such as computer 120 of FIG. 1).

Sensor engine 924 may receive information related to the motion sensors 910 and analyze and/or otherwise process the motion sensor information. For example, sensor engine 924 may receive sensor information indicative of one or more objects that are moving within the proximate view of one or more motion sensors 910. The sensor engine 924 may determine, based on one or more methods, which objects that are identifiable from the data are users of the system and then track those users. In some implementations, sensor engine 924 may utilize information from one or more other components to determine which moving objects are users. For example, sensor engine 924 may additionally utilize a signal from a personal device 905 to determine that a user is present, where the user is present, and/or an indication of one or more movements that are currently being performed by the user (that may be detected via, for example, a movement sensor 906).

Registration monitor 922 may receive image information from the sensor engine 924 that indicates that a user is present for identification. In some implementations, the user may first activate the personal device 905 to send a signal to sensor engine 924 indicating that the associated user desires to be tracked by the system. The sensor engine 924 may then monitor the images being received from the motion sensors 910 to start to identify the user. In some implementations, the user may be required to perform a particular movement to signal to the sensor engine 924 which is the user from a plurality of potential objects that may be the user. For example, the user may hold his hands up in a particular position and/or make some other bodily movement that may be assist the sensor engine 924 in identifying the user.

The registration monitor 922 may identify information related to the now-tracked user in database 915. The registration monitor 922 may identify, for example, the user's name, personal information, information regarding previous tracking sessions, biometric information, and/or other information that may be utilized in conjunction with monitoring the user's movements during the session. In some implementations, the signal from the personal device 905 may indicate which user is being tracked and that information may be utilized by the registration monitor 922 to identify user information in database 915. In some implementations, registration monitor 922 may utilize image information from the sensor engine 924 to identify potential users from the image data, and then utilize defining characteristics of the user (e.g., biometrics) to identify the user.

Metric recorder 928 may utilize the motion sensor information related to a tracked user to determine the movements of the user. In some implementations, the metric recorder 928 will only track the movements of users who have been registered with the system. For example, referring to FIG. 1, worker 130 and worker 140 may be tracked by the system and metric recorder 928 may record and monitor their movements, whereas patient 150 may not be monitored because the patient 150 has not registered with the system. In this way, the system 920 may monitor movements of some objects without invading privacy of any users who do not wish to or have not consented to being monitored.

Figure 1:
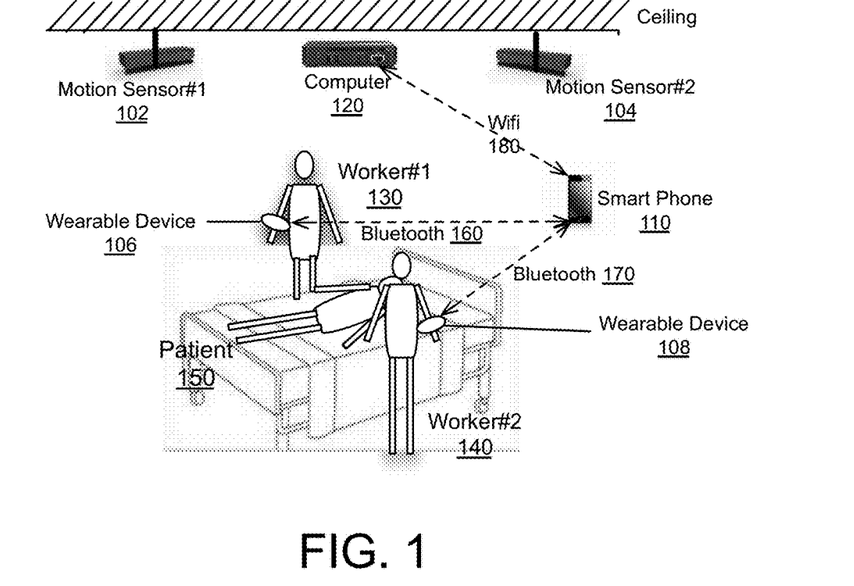
FIG. 1 is an exemplary environment for an implementation of the present invention.

Metric recorder 928 may utilize motion information to determine the movements of users. For example, metric recorder 928 may identify the limbs of the monitored user, the joint locations of the monitored users, the location of key body parts of the user, the location of the user in a room, and/or other information related to the movements of the tracked users. For example, the worker 130 may start from a first position, approach the patient 150, and move the patient 150 in some way. Metric recorder 928 may identify each of these movements based on the image information.

Alert engine 926 may receive metrics of the movements of users from metric recorder 928 and may analyze the movements to determine if the user has performed, in the process of performing, and/or is about to perform an improper movement. For example, worker 130 may squat down to pick up a large object. Metric recorder 928 may identify the movements of the user and transmit the movement information to alert engine 926. If the alert engine 926 identifies that the user is in a position that may result in an injury, the alert engine 926 may produce an alert signal. The alert signal may result in, for example, a haptic alarm on the personal device 905, an audible alarm, a visual warning, and/or one or more other types of alarms.

FIGS. 1 through 8 illustrate additional implementations of the system. In some implementations, components similar or identical to components of the system illustrated in FIG. 9 may be utilized in FIGS. 1 to 8. In some implementations, one or more processes and/or steps may be performed by an alternate component and/or hardware system. The embodiments described herein are merely an additional explanation of the present invention and may be utilized in conjunction with or as an alternative to any component of FIG. 9.

FIG. 1 illustrates a system according to one embodiment of the present invention. The system comprises one or more computer-vision based motion tracking sensors 102 and 104 (which may share one or more characteristics with motion sensors 1010), one or more human subjects 130 and 140 that have been consented to being monitored, one or more wearable devices 106 and 108 worn by consenting human subjects (which may share one or more characteristics with personal device 1005), one or more smart phones 110 (which may execute one or more components of personal device 1005 and/or system 1020), and a computer 120 (which may execute one or more of the components of system 1020). Non-consenting human subjects 150 might be present in the view of the vision-based motion sensors 102 and 104. The wearable devices 106 and 108 communicate with the smart phone 110 via low-energy Bluetooth 160 and 170, and the smart phone 110 relays the messages received to the computer 120 via 802.11 (wifi) wireless communication protocols 180.

Figure 2:
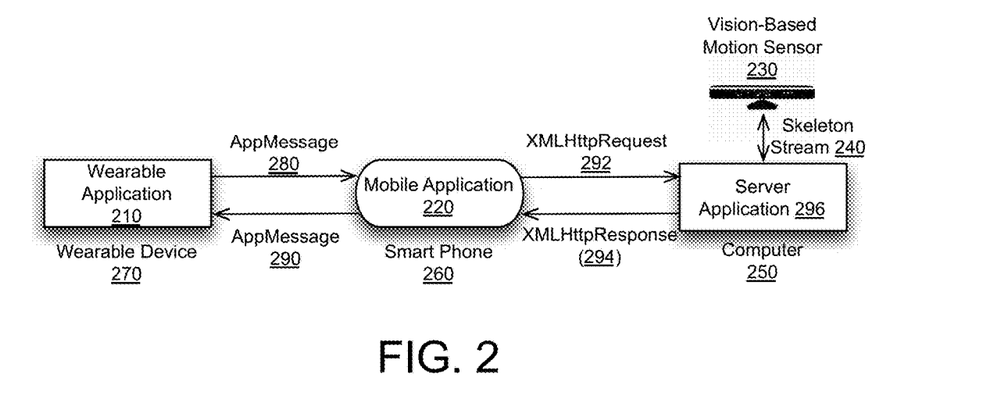
FIG. 2 is a diagram illustrating the interaction pattern between different software components in accordance with one embodiment of the present invention.

FIG. 2 illustrates the software components in the system and how they interact with each other. A wearable application 210 runs on each wearable device 270. The wearable application 210 has two-way communications with a mobile application 220 running on the smart phone 260. The mobile application 220 has two-way communications with the server application 296 running on the computer 250. The server application 296 receives motion-sensing data collected by the motion sensor 230 attached to the computer 250, such as the skeleton stream 240. Typically, a programmable computer-vision based motion sensor provides at least four types of frames to the server application, including the color frames showing color images of its view, infrared (IR) frames showing the images collected by its IR camera, depth frames that contains the distance of each pixel from the sensor, and the skeleton (also referred to as body) frames that contains the skeleton joints of each tracked human subject. The number of consenting human subjects can be tracked by the system is limited by the type of motion sensors and the number of motion sensors used.

The communication loop between the three main software components 210, 220, and 296 is driven by the wearable application 210. During registration, the wearable application 210 sends a registration request message 280 to the mobile application 220 upon detection of a predefined gesture using the accelerometers equipped with the wearable device 270. The mobile application 220 would then relay the registration request in message 292 to the server application 296. The server application 296 then examines the next frame or the cached set of frames 240 to determine whether or not the corresponding gesture is performed by any of the fully tracked users. If one and only one user is detected, the registration succeeds and the server application 296 labels that particular user as being monitored from now on. The status of the registration will be included in messages 294 and 290. Upon receiving message 290, the wearable application 210 generates an appropriate vibration and short message for display according to the result of the registration request.

The server application 296 continuously monitors all registered human subjects and logs detected violations of best practices including the nature of the violation and the timestamp of the incidence in its own durable storage as well as its memory (RAM). The server application 296 may additionally monitor other information regarding registered human subjects, such as the duration, starting and ending timestamps, of each registration session, as well as the number of activities that have been carried out successfully for each registered subject.

Each tracked user by the motion sensor is assigned a unique user identifier. When a user leaves the view of the motion sensor, the corresponding skeleton (or body) cedes to exist in the depth and skeleton (or body) frames. Therefore, the monitoring would naturally stop when the registered user leaves the view of the motion sensor. If the previously registered user comes back to the view of the motion sensor, the motion sensor assigns a new user identifier to the user, thereby necessitating a new round of registration before the user can be monitored again.

After a human subject successfully registers with the system, the communication loops continues to operate. The wearable application 210 periodically polls the mobile application 220, which in turn queries the server application 296. Upon receiving message 292, the server application returns the status of the subject. In turn, the mobile application 220 relays the response to the wearable application 210 in the message 290. If a violation is detected, the wearable application 270 generates a vibration and displays a corresponding message on the display of the wearable device, if one is available.

Figure 3:
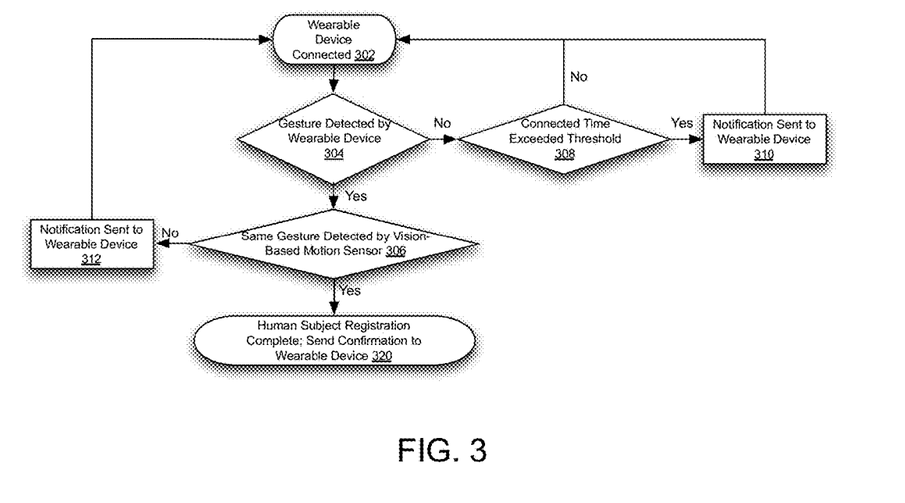
FIG. 3 is flow chart illustrating the registration mechanism components in accordance with one embodiment of the present invention.

FIG. 3 illustrates a flow chart of an exemplary registration method. In some embodiments, the wearable application 210 (in FIG. 2) drives the registration process. The wearable application 210 (in FIG. 2) may receive a notification when the wearable device 270 is able to establish a communication connection to the smart phone 260 (in FIG. 2). The wearable application 210 (in FIG. 2) may then launch the registration method described in FIG. 3 when it learns that the wearable device is in the connected state 302. The wearable application 210 (in FIG. 2) receives accelerometer-related data and events from the wearable device 270. Based on the collected information, the wearable application may detect whether or not a predefined gesture has happened. If such a gesture is detected 304, the wearable application 210 (in FIG. 2) may send a registration request to the server application 296 (in FIG. 2) via the mobile application 220 (in FIG. 2). The server application then tries to detect the corresponding gesture based on the next frame or the cached frames. If one is detected 306, in step 320, the server application 296 (in FIG. 2) may generate a corresponding response and send the response to the wearable application 210 (in FIG. 2) via the mobile application 220 (in FIG. 2).

If the server application 296 (in FIG. 2) fails to detect the corresponding gesture, or it detects two of more users in its view that have performed the same gesture, the registration may fail and a failure notification may be sent to the wearable application 210 (in FIG. 2) in step 312.

In some instances, a consenting human subject may forget to register upon arriving at a predefined location. In those instances, the wearable application 210 (in FIG. 2) may take a timestamp when it learns that the wearable device 270 (in FIG. 2) has connected to the smart phone 260 (in FIG. 2), and furthermore maintain a configurable threshold for registration. Periodically, the wearable application 210 (in FIG. 2) may monitor the time that has elapsed before the registration is completed. If the time elapsed since an initial communication connection exceeds the threshold in step 308, the wearable application 210 (in FIG. 2) may generate a notification in the form of a vibration and/or a short message for display in step 310.

Figure 4:
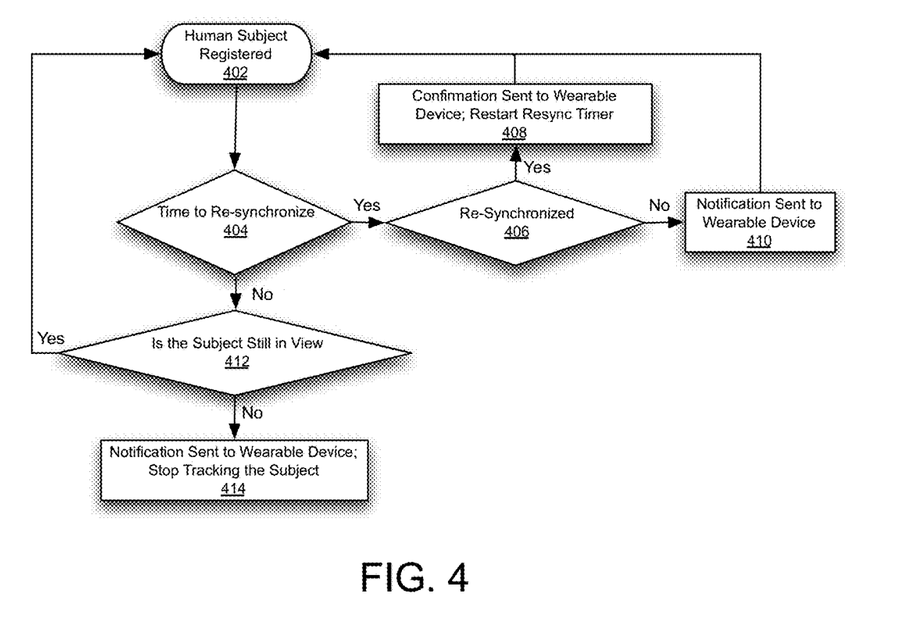
FIG. 4 is a flow chart illustrating the re-synchronization mechanism when the system is in a registered state for a consenting human subject in accordance with one embodiment of the present invention.

FIG. 4 illustrates a flow chart of a method to periodically re-register a consenting human subject (referred to as re-synchronization). Additionally, the flow chart illustrates steps that may be utilized when a registered subject leaves the view of the vision-based motion sensor. When a human subject has registered 402, the wearable device 210 (in FIG. 2) periodically monitors to determine whether re-registration is required (step 404). The wearable device 210 (in FIG. 2) may record a timestamp in memory each time the subject successfully registers. The wearable application 210 (in FIG. 2) maintains another configurable parameter as the threshold for re-registration. If the time since the last recorded timestamp satisfies the registration threshold parameter at re-registration 404, the wearable application 210 (in FIG. 2) monitors for the subject to perform a predefined gesture. If the requisite gesture is detected and it is successful 406, the timestamp is updated and a confirmation is generated 408. Otherwise, a notification for re-registration is generated 410.

The server application 296 (in FIG. 2) monitors whether or not the subject is still in its view 412. If the registered human subject is no longer in its view, the server application 296 (in FIG. 2) logs the event. The wearable application 210 (in FIG. 2) would learn this status change the next time it polls the server application 296 (in FIG. 2). It subsequently generates a notification for the subject to register again 414 when the wearable device is connected to the smart phone.

Figure 5:
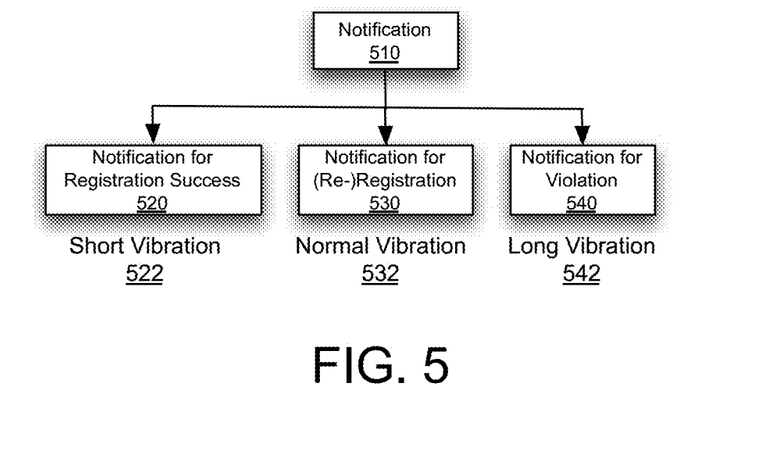
FIG. 5 is a diagram illustrating different types of notifications generated by the system in accordance with one embodiment of the present invention.

FIG. 5 shows three types of haptic feedback 510 that may be used in the system in one embodiment of the present invention. A programmable wearable device typically offers different levels of haptic feedback in terms of the duration and/or intensity of generated vibrations. For example, if such a device offers three levels of haptic feedback, as does in the Pebble Smart Watch, the system may use a short vibration 522 for notification of successful registration 520, a normal vibration 532 for notification for a human subject to register or re-register 530, and a long vibration 542 for notification of a violation of best practices. Also, for example, if a wearable device has two levels of haptic feedback, then notification 520 and notification 530 could both use the same shorter vibration and the long vibration may be utilized for notification 540.

Figure 6:
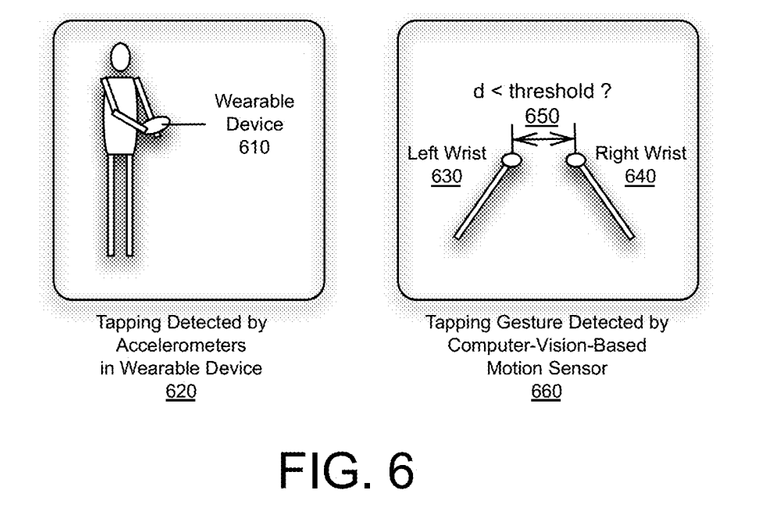
FIG. 6 is a diagram illustrating an example gesture that could be used to register a human subject to the system in accordance with one embodiment of the present invention.

FIG. 6 illustrates one particular gesture that can be used for registration. Other gestures could be designed for the purpose of registration. To register, a human subject could tap his or her wearable device 610 worn on his or her left or right wrist using the finger of the other hand. The tapping event may be detected by accelerometers in the wearable device 620 and/or via one or more other sensors. When a subject begins to motion to tap his or her wearable device, the distance between the left and right wrists 630 and 640 will decrease. In some embodiments, the computer-vision based motion sensor could detect this gesture by determining the wrist-to-wrist distance with respect to a configurable threshold parameter. If the wrist-to-wrist distance is smaller than a threshold value 650, then the vision-based motion sensor detects the tapping gesture 660 using a single frame. In instances where another non-consenting human subject is in the view of the motion sensor, he or she might also satisfy the wrist-to-wrist distance criteria (i.e., the wrists of the non-consenting human may be close together, but not intended to be positioned for registration purposes). As the result, the motion sensor might find that two or more users have performed the tapping gesture. In this case, the registration would fail because the motion sensor would be unable to determine which of the detected humans has consented to monitoring.

In some instances, the consenting subject (i.e., the one intending to register) may be occluded by a non-consenting subject, and the wrong subject may be registered. To minimize the probability of this from happening, the entire tapping gesture could be recognized by the server application. The tapping gesture involves two monotonic movement segments: (1) the wrist-to-wrist distance is reduced from a value larger than a predefined value down to below a threshold value as the wearer moves one hand closer to the other to tap; and (2) after a momentary pause at a minimum wrist-to-wrist distance (for tapping), the wrist-to-wrist distance increases beyond a predefined value. To capture the entire tapping gesture, a set of frames that expand the duration of the gesture may be cached. As an example, if the motion sensor has a frame rate of 30 per second and the gesture takes 2 seconds, then 60 frames will need to be cached.

Figure 7:
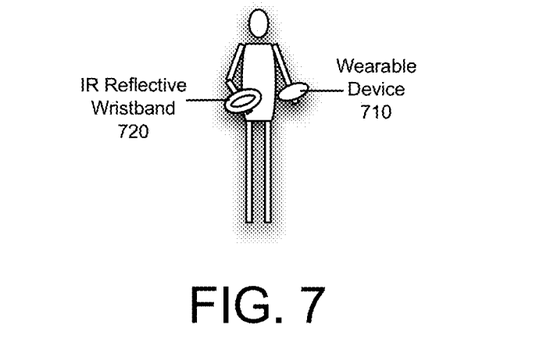
FIG. 7 is a diagram illustrating an alternative method for automated registration without using any gesture.

FIG. 7 illustrates an alternative method for registration. In this method, consenting human subject wears a wristband that includes an infrared reflective material 720 in addition to a wearable device 710. In some embodiments, only consenting human subjects may wear such a wristband. The computer-vision based motion sensor performs object recognition for the wristband in every depth frame received. If such a wristband is detected, then the user who wears the wristband is automatically registered and monitored. The programmable wearable device 710 is still needed for driving the monitoring system and for user notification of violations of best practices.

Figure 8:
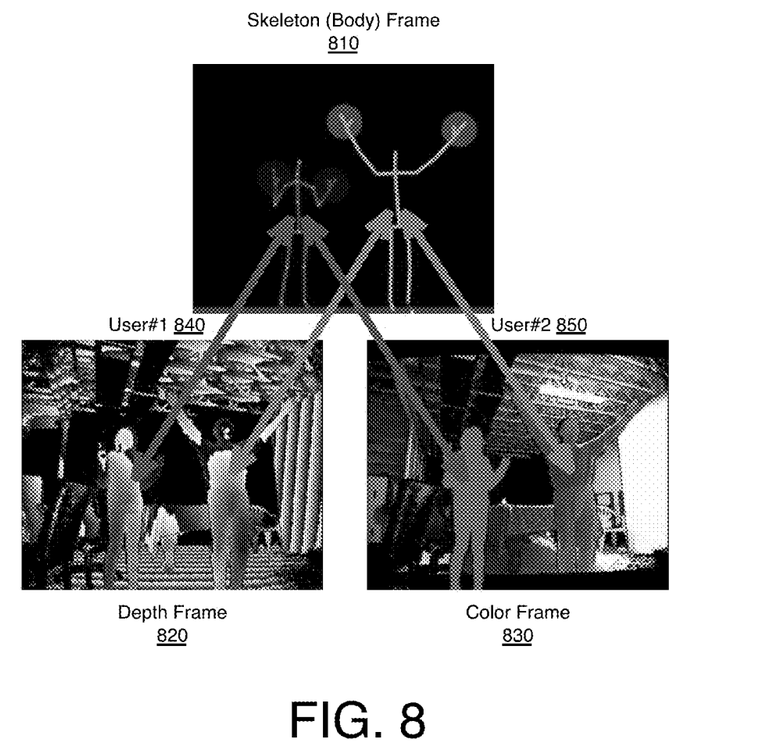
FIG. 8 is a diagram illustrating how to anonymize non-consenting human subjects in color frames in accordance with one embodiment of the present invention.

FIG. 8 illustrates how to anonymize non-consenting human subjects in color frames in accordance with one embodiment of the present invention. Each tracked user is assigned a unique user identifier, such as user #1 840 and user #2 850. The user identifier is encoded in both the skeleton (or body) frame 810 and the corresponding depth frame 820. User identifier information is not included in color frames 830. However, in the depth frame 820, every pixel contains user identifier information 840 and 850. If a pixel does not belong to any user tracked by the motion sensor, it may include a predefined value indicating that the pixel belongs to the profile of a non-tracked individual. Furthermore, the depth pixel position can be mapped to that of the color frame. Based on this mapping, one can associate each color pixel that is within the range of the depth frame (because the color frame might be set to a higher resolution than that of the depth frame) to any user tracked by the motion sensor. One can further identify which color pixel belongs to the registered human subject. With such identification information, color pixels that belong to non-consenting human subjects 840 can be rendered a monotonic color, or any desirable color pattern, while color pixels that belong to the registered human subject 850 can keep the original colors.

While particular embodiments and applications of the present invention have been illustrated and described herein, it is to be understood that the invention is not limited to the precise construction and components disclosed herein and that various modifications, changes, and variations may be made in the arrangement, operation, and details of the methods and apparatuses of the present invention without departing from the spirit and scope of the invention as it is defined in the appended claims.

What is claimed is:

1. A system to monitor only consenting human subjects, comprising:
   one or more computer-vision based programmable motion sensors;
   one or more programmable wearable devices;
   one or more smart phones; and
   one or more processors;
   wherein the one or more computer-vision based programmable motion sensors identifies a consenting human subject that is wearing one of the programmable wearable devices;
   wherein the one or more computer-vision based programmable motion sensors identifies a non-consenting human subject;
   wherein the one or more processors ignores the non-consenting human subject;
   wherein the one or more processors monitors the consenting human subject for violations of best practices; and
   wherein the one or more processors provides violation alerts to the consenting human subject when a violation is detected.

2. The system of claim 1, further comprising:
   a wristband that includes an infrared reflective material, wherein the wristband is worn only by consenting human subjects; and wherein the one or more computer-vision based programmable motion sensors identifies the consenting human subject by identifying the wristband.

3. A method for identifying a consenting human subject, comprising:
   recognizing, via one or more sensors, a predefined gesture performed by a consenting human subject, the consenting human subject wearing a detectable wearable device;
   providing a registration request, the registration request including an indication that the consenting human subject has interest in being monitored;
   receiving vision-based motion data from one or more motion sensors;
   recognizing a gesture by the consenting human subject from the vision-based motion data; and
   providing a confirmation message to the consenting human subject via haptic feedback and a short message displayed on the wearable device.

4. The method of claim 3, wherein the gesture is a tapping motion on the wearable device by one or more fingers of the opposite hand, wherein the gesture is detected by one or more accelerometers in the wearable device, and wherein, once the gesture is detected, recognizing the gesture includes comparing the wrist-to-wrist distance against a predefined configurable threshold.

5. The method of claim 4, wherein recognizing the gesture includes:
caching one or more skeleton frames; and
utilizing the cached frames to determine the occurrence of the gesture.

6. The method of claim 3, wherein the wearable device includes an infrared-reflective surface, and wherein the gesture is further recognized utilizing the infrared-reflective surface.

7. The method of claim 3, further comprising:
providing an alert message via haptic feedback and short message displayed on the wearable device when the consenting human subject is not recognizable via the one or more sensors.

8. The method of claim 3, further comprising:
providing an alert message via haptic feedback and short message displayed on the wearable device when the consenting human subject is recognizable via the one or more sensors the human subject has not performed the gesture.

9. The method of claim 3, further comprising:
recording a registration time, wherein the registration time is associated with the registration request;
monitoring the current time; and
providing a re-registration message when a different between the current time and the registration satisfies a threshold re-registration period.

10. The method of claim 3, further comprising:
monitoring the sensor data;
detecting that the consenting human subject was not viewable by the sensors for a threshold period and is currently viewable by the sensors; and
and providing a re-registration message.

11. The method of claim 3, further comprising:
identifying a non-consenting human subject via the sensors; and
altering one or more pixels associated with the non-consenting human subject in color frames that depict the non-consenting human subject.

12. A system for alerting a person of improper actions, the system comprising:
a plurality of motion sensors, wherein the motion sensors communicate to send a stream of images of a viewing area of the motion sensors;
a wearable device, wherein the wearable device is associated with the user and capable of sending and receiving a signal, the signal indicative of the person in a field of view of the motion sensors; and
a central processor, wherein the central processor:
receives the signal from the wearable device indicating the presence of the person in the viewing area;
monitors the images from the motion sensors to identify the person, wherein the person is identified in one or more of the images by one or more specific movements of the person;
tracks one or more orientations of the person;
identifies an improper orientation from the one or more orientations of the person; and
sends a warning signal based on the identified improper orientation.

13. The system of claim 12, wherein monitoring the images from the motion sensors includes:
identifying one or more non-consenting subjects in the images; and
ignoring movements of the non-consenting subjects.

14. The system of claim 13, wherein ignoring movements of the non-consenting subjects includes:
altering one or more pixels associated with the non-consenting subject in color frames that depict the non-consenting human subject.

15. The system of claim 12, wherein the improper orientation is the person improperly picking up an object.

16. The system of claim 12, wherein the improper orientation is determined based on one or more joint positions of the person.

17. The system of claim 12, wherein the warning signal is received by the wearable device.

18. The system of claim 17, wherein the warning signal is utilized by the wearable device to transmit a haptic feedback signal.

19. The system of claim 12, wherein the wearable device is a smart watch.

20. A method for alerting a person of improper actions, comprising:
receiving, from one or more user devices, an indication that a user is present in a viewing area;
activating, in response to receiving the indication, one or more motion sensors to monitor the viewing area;
receiving image data from the one or more sensors;
analyzing the image data to identify the user;
tracking the movements of the user based on the image data;
identifying a posture that is indicative of potential harm to the user; and
sending a warning signal to one or more alert systems.

* * * * *